United States Patent [19]
Bandman et al.

[11] Patent Number: 5,965,394
[45] Date of Patent: Oct. 12, 1999

[54] HUMAN IMPORTIN ALPHA HOMOLOG

[75] Inventors: Olga Bandman, Mountain View; Karl J. Guegler, Menlo Park; Neil C. Corley, Mountain View; Purvi Shah, Sunnyvale, all of Calif.

[73] Assignee: Incyte Pharmaceuticals, Inc., Palo Alto, Calif.

[21] Appl. No.: 08/933,227

[22] Filed: Sep. 18, 1997

[51] Int. Cl.[6] .............................. C12P 21/06; C12N 5/00; C12N 15/00; C07H 17/00
[52] U.S. Cl. .............................. 435/69.1; 435/6; 435/325; 435/320.1; 435/252.3; 536/23.1
[58] Field of Search .......................... 536/23.1; 435/69.1, 435/6, 325, 320.1, 252.3

[56] References Cited

PUBLICATIONS

Moroianu et al. 1995 PNAS 92:6532–6536.

*Primary Examiner*—Karen Cochrane Carlson
*Attorney, Agent, or Firm*—Incyte Pharmaceuticals Inc.; Sheela Mohan-Peterson; Lucy J. Billings

[57] ABSTRACT

The invention provides a human importin alpha homolog (IMPAH) and polynucleotides which identify and encode IMPAH. The invention also provides expression vectors, host cells, agonists, antibodies and antagonists. The invention also provides methods for treating disorders associated with expression of IMPAH.

10 Claims, 9 Drawing Sheets

```
                                      9                18           27        36        45        54
5'  G  CCG  GAG  CCG  GCA  GCC  CGC  GCA  GCC  CGC  ATG  GCC  GAG  AAC  CCC  AGC  TTG  GAG  AAC  CAC
                                                       M    A    E    N    P    S    L    E    N    H 63           72            81            90            99           108
CGC  ATC  AAG  AGC  TTC  AAG  AAC  AAG  GGC  GAA  CTG  GAT  GTG  GAA  ACA  ATG  CGA  AGA  CAT
 R    I    K    S    F    K    N    K    G    E    L    D    V    E    T    M    R    R    H 117          126           135           144           153           162
AGA  GAA  GTG  ACA  GTG  CGG  AAG  AAC  AGA  AGA  GAT  GAA  CAC  TTA  TTG
 R    E    V    T    V    R    K    N    R    R    D    E    H    L    L 171          180           189           198           207           216
AAA  AGA  AAT  GTT  CCC  CAA  GAA  AGT  CTA  GAA  GAT  TCA  GAT  GTT  GAT  GCT
 K    R    N    V    P    Q    E    S    L    E    D    S    D    V    D    A 225          234           243           252           261           270
GAT  TTT  AAA  GCA  CAA  AAT  GTA  ACC  CTA  GAA  GCT  ATA  TTG  CAG  AAT  GCC  ACA  AGT
 D    F    K    A    Q    N    V    T    L    E    A    I    L    Q    N    A    T    S 279          288           297           306           315           324
GAT  AAC  CCA  GTG  GTC  CAA  TTG  AGT  GCT  GTC  CAG  GCA  GCA  AGA  AAA  CTG  TTA  TCC
 D    N    P    V    V    Q    L    S    A    V    Q    A    A    R    K    L    L    S 333          342           351           360           369           378
AGT  GAC  AGA  AAT  CCA  CCG  ATT  GAT  GAC  TTA  ATA  AAA  TCT  GGG  ATT  TTA  CCA  ATT
 S    D    R    N    P    P    I    D    D    L    I    K    S    G    I    L    P    I

FIG. 1A
```

```
387                396     405     414     423     432
CTA GTC AAA TGT CTA GAA AGG GAT AAT CCT TCA TTA CAG TTT GAA GCT
 L   V   K   C   L   E   R   D   N   P   S   L   Q   F   E   A 441                450     459     468     477     486
TGG GCA TTA ACT AAC ATA GCA TCA GGA ACT TCT GCA CAG ACT CAA GCT GTT GTG
 W   A   L   T   N   I   A   S   G   T   S   A   Q   T   Q   A   V   V 495                504     513     522     531     540
CAG TCT AAT GCA GTA CCT CTT TTT CTG AGA CTT CGT TCA CCA CAT CAG AAT
 Q   S   N   A   V   P   L   F   L   R   L   R   S   P   H   Q   N 549                558     567     576     585     594
GTT TGT GAA CAA GCA GTA TGG GCT TTG GGA AAC ATT ATA GGT GAT GGT CCT CAA
 V   C   E   Q   A   V   W   A   L   G   N   I   I   G   D   G   P   Q 603                612     621     630     639     648
TGT AGA GAT TAT GTC ATA TCA CTG GGA GTT GTC AAA CCT CTT TCC TTC ATC
 C   R   D   Y   V   I   S   L   G   V   V   K   P   L   S   F   I 657                666     675     684     693     702
AGT CCC ATC ACC TTC CTT CGG AAC GTC ACA TGG GTC ATT GTC AAT
 S   P   I   T   F   L   R   N   V   T   W   V   I   V   N 711                720     729     738     747     756
CTC TGC AGG AAT AAG GAT CCC CCA CCG CCT ATG GAG ACA GTT CAG GAG ATT TTG
 L   C   R   N   K   D   P   P   P   P   M   E   T   V   Q   E   I   L
```

FIG. 1B

```
CCA GCT TTA TGT GTC ATA TAC CTC ACA GAT CAT ATA AAC ATT CTT GTA GAC ACT
 P   A   L   C   V   I   Y   L   T   D   H   I   N   I   L   V   D   T
765         774         783         792         801         810

GTT TGG GCT CTG TCA TAC TTG ACA GAT GGA GGT AAT GAA CAG ATA CAG ATG GTT
 V   W   A   L   S   Y   L   T   D   G   G   N   E   Q   I   Q   M   V
819         828         837         846         855         864

ATT GAT TCA GGA GTT GTG CCC TTT CTT GTG CCC CTT AGC CAT CAG GAA GTC
 I   D   S   G   V   V   P   F   L   V   P   L   S   H   Q   E   V
873         882         891         900         909         918

AAA GTT CAA ACA GCA GCC CTC AGA GCA GTT GGC AAC ATA GTG ACT GGC ACC GAC
 K   V   Q   T   A   A   L   R   A   V   G   N   I   V   T   G   T   D
927         936         945         954         963         972

GAG CAG ACC CAG GTT CTC AAT TGT GAT GTC CTG TCA CAC TTC CCA AAT CTC
 E   Q   T   Q   V   L   N   C   D   V   L   S   H   F   P   N   L
981         990         999         1008        1017        1026

TTA TCA CAC CCA AAA GAG AAG ATA AAT AAG GAA GCA GTG TGG TTC CTT TCC AAC
 L   S   H   P   K   E   K   I   N   K   E   A   V   W   F   L   S   N
1035        1044        1053        1062        1071        1080

ATA ACA GCA GGC AAC CAG CAA CAA GTT CAA GCT GTA ATA GAT GCT GGA TTA ATT
 I   T   A   G   N   Q   Q   Q   V   Q   A   V   I   D   A   G   L   I
1089        1098        1107        1116        1125        1134
```

FIG. 1C

```
       1143           1152           1161           1170           1179           1188
CCT ATG ATA ATT CAT CAG CTT GCT AAG GGG GAC TTT GGA ACA CAA AAA GAA GCT
 P   M   I   I   H   Q   L   A   K   G   D   F   G   T   Q   K   E   A 1197           1206           1215           1224           1233           1242
GCT TGG GCA ATC AGC AAC TTA ACA ATA AGT GGC AGA AAA GAT CAG GTT GAG TAC
 A   W   A   I   S   N   L   T   I   S   G   R   K   D   Q   V   E   Y 1251           1260           1269           1278           1287           1296
CTT GTA CAG CAG AAT GTA ATA CCA CCG TTC TGT AAT TTA CTG TCA GTG AAA GAT
 L   V   Q   Q   N   V   I   P   P   F   C   N   L   L   S   V   K   D 1305           1314           1323           1332           1341           1350
TCT CAA GTG GTT CAG GTG GTT CTA GAT GGT CTA AAA AAC ATT CTG ATA ATG GCC
 S   Q   V   V   Q   V   V   L   D   G   L   K   N   I   L   I   M   A 1359           1368           1377           1386           1395           1404
GGT GAT GAA GCA AGC ACA ATA GCT GAA ATA ATA GAG GAA TGT GGA GGT TTG GAG
 G   D   E   A   S   T   I   A   E   I   I   E   E   C   G   G   L   E 1413           1422           1431           1440           1449           1458
AAA ATT GAA GTT TTA CAG CAA CAT GAA AAT GAA GAC ATA TAT AAA TTA GCA TTT
 K   I   E   V   L   Q   Q   H   E   N   E   D   I   Y   K   L   A   F 1467           1476           1485           1494           1503           1512
GAA ATC ATA GAT CAG TAT TTC TCT GGT GAT GAT ATT GAT GAA GAT CCC TGC CTC
 E   I   I   D   Q   Y   F   S   G   D   D   I   D   E   D   P   C   L
```

FIG. 1D

```
      1521           1530           1539          1548          1557           1566
ATT CCT GAA GCA ACA CAA GGA GGT ACC TAC AAT TTT GAT CCA ACA GCC AAC CTT
 I   P   E   A   T   Q   G   G   T   Y   N   F   D   P   T   A   N   L 1575           1584           1593          1602          1611           1620
CAC ACA AAA GAA TTT AAT TTT TAA ATT CAG TTG AGT GCA GCA TCT TTC CCA CAT
 H   T   K   E   F   N   F 1629           1638           1647          1656          1665           1674
TCA ATA TGA AGC ACC ACC AGA TGG CTA CCA AAT GAT AAG AAC ACA GCC ACA AAA 1683           1692           1701          1710          1719           1728
AGC TCC CAA ACA CAC ATG CCT CTT TGG TTT GAT GCT TCT AAG GCA GCC ATG TCT

CAG CCC T 3'
```

HUMAN IMPORTIN ALPHA HOMOLOG

FIELD OF THE INVENTION

This invention relates to nucleic acid and amino acid sequences of a human importin alpha homolog and to the use of these sequences in the diagnosis, prevention, and treatment of disorders associated with cell proliferation, viral infection, and the immune response.

BACKGROUND OF THE INVENTION

Transport of proteins and RNA between the nucleus and the cytoplasm occurs through nuclear pore complexes (NPCs). NPC-mediated transport occurs in both directions through the nuclear envelope. All nuclear proteins are imported from the cytoplasm, their site of synthesis. Transfer RNA (tRNA) and messenger RNA (mRNA) are exported from the nucleus, their site of synthesis, to the cytoplasm, their site of function. Furthermore, the biogenesis of the ribonucleoproteins involves multiple transport steps. Processing of small nuclear RNAs (snRNAs) involves export into the cytoplasm, assembly with Sm proteins and modifications such as hypermethylation to produce small nuclear ribonuclear proteins (snRNPs), and subsequent import of the snRNPs back into the nucleus. The assembly of ribosomes requires the initial import of ribosomal proteins from the cytoplasm, their incorporation with RNA into ribosomal subunits, and export back to the cytoplasm. Görlich, D. and Mattaj, I. W. (1996; Science 271:1513–1518) estimated that in a HeLa cell which divides every 24 hours, approximately 100 ribosomal proteins and 3 ribosomal subunits must travel through a single NPC per minute.

The transport of proteins and RNPs across the NPC is generally selective and signal-dependent. Nuclear localization sequences (NLSs) are usually characterized by one or more clusters of basic amino acids, but they do not conform to a tight consensus (Görlich and Mattaj, supra). For instance, the NLS of the large T antigen of simian virus 40 (SV40) was initially found by point mutations which misdirected the protein to the cytoplasm. The SV40 T antigen NLS is a seven amino acid sequence which is sufficient to confer nuclear localization even when conjugated as a synthetic polypeptide to another protein such as serum albumin. Saturation of the protein import pathway by microinjection of high concentrations of NLS-peptide conjugates provided strong evidence for the existence of saturatable NLS receptors. Experimental evidence suggests that there are multiple receptors for different NLS-containing protein substrates (Görlich and Mattaj, supra).

The NPCs, or nucleoporins, are estimated to contain about 100 different polypeptides. A heterodimeric protein complex consisting of importin alpha and importin beta (also known as karyopherin alpha and beta) targets the NLS-containing substrate proteins to the NPCs. The alpha subunit of importin functions as the NLS receptor, whereas the beta subunit mediates docking to the NPC. The small GTPase Ran mediates the energy-dependent translocation of the substrate-receptor complex through the NPC. After translocation, the importin heterodimer dissociates: importin alpha and the substrate enters and accumulates in the nucleoplasm, and importin beta accumulates at the nuclear pore complex. Ran-GTP induces the dissociation of the importin subunits by forming a complex with importin beta (Görlich and Mattaj, supra). Multiple importin-alpha homologs have been identified in mouse and in man (Weis, K. et al (1995) Science 268:1049–1053; Seki, T. et al. (1997) Biochem. Biophys. Res. Comm. 234:48–53).

Defective nuclear transport plays a role in cancer. The BRCA1 protein contains three potential NLSs which interact with importin alpha and is transported into the nucleus by the importin/NPC pathway. Recently, Chen, C. F. et al. (1996; J. Biol. Chem. 271:32863–32868) reported that in breast cancer cells the BRCA1 protein is aberrantly localized in the cytoplasm. Wild-type BRCA1 protein expressed in six different breast cancer cell lines was localized in the cytoplasm. However, wild-type BRCA1 protein expressed in four non-breast cancer cell lines was localized in the nucleus. Chen et al. (supra) proposed that the mislocation of the BRCA1 protein in breast cancer cells may be due to a defect in the importin/NPC nuclear import pathway.

Moll, U. M. et al. (1992; Proc. Natl. Acad. Sci. USA 89:7262–7266) demonstrated that in 10 of 27 cases of breast cancer, p53 tumor suppressor protein was found in the cytoplasm. A majority of the p53 cDNAs derived from breast cancers with cytoplasmic p53 protein were wild type. In contrast, p53 cDNAs derived from breast cancers with nuclear p53 protein contained a variety of missense mutations and a nonsense mutation. Moll et al. (supra) suggested that in some breast cancers, the tumor-suppressing activity of p53 is inactivated by the sequestration of the protein in the cytoplasm, away from its site of action in the cell nucleus. Furthermore, the presence of wild-type p53 in the cytoplasm of normal lactating breast tissue suggested that this mechanism may be employed in specific physiologic situations to permit transient cell proliferation. Cytoplasmic wild-type p53 was also found in human cervical carcinoma cell lines (Liang, X. H. et al. (1993) Oncogene 8:2645–2652).

Nuclear transport by the importin/NPC pathway also plays a role in infection by HIV and other viruses. HIV can infect nondividing cells (such as terminally differentiated macrophages, mucosal dendritic cells, and quiescent T-lymphocytes) because its preintegration complex is recognized by and is actively transported through the NPC. The uncoated HIV-1 preintegration complex contains three proteins, matrix protein MA, Vpr, and integrase IN, known to contain NLSs which interact with importin alpha and which play important roles in the nuclear import and the viral integration processes (Gallay, P. et al. (1997) Proc. Natl. Acad. Sci. USA 94:9825–9830). Furthermore, the NLS-dependent nuclear import activity of the HIV preintegration complex permits the in vivo delivery of transgenes by HIV-derived retroviral vectors into terminally differentiated cells such as neurons. In contrast, oncoretroviruses such as the murine leukemia virus and oncoretroviral vectors cannot traverse an intact nuclear envelope, which precludes their integration into nondividing cells (Gallay et al., supra).

Epstein-Barr virus (EBV) is the etiological agent of infectious mononucleosis and the putative inductive agent of several malignancies. The EBV nuclear antigen-1 (EBNA1), the only EBV protein necessary for replication and maintenance of the EBV genome in the infected cell, interacts with importin alpha through its NLS and is transported into the nucleus by the importin/NPC pathway (Fisher, N. et al. (1997) J. Biol. Chem. 272:3999–4005). Other viral proteins known to contain NLSs include nucleoprotein and the RNA polymerase subunits of influenza virus; VP1, VP2, and VP3 proteins of SV40; and hexon and several coat proteins of adenovirus (Gallay et al., supra).

The discovery of a new human importin alpha homolog and the polynucleotides encoding it satisfies a need in the art by providing new compositions which are useful in the diagnosis, prevention, and treatment of disorders associated with cell proliferation, viral infection, and the immune response.

SUMMARY OF THE INVENTION

The invention features a substantially purified polypeptide, human importin alpha homolog (IMPAH), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2 . The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding IMPAH under conditions suitable for the expression of the polypeptide; and b) recovering the polypeptide from the host cell culture.

The invention also provides a pharmaceutical composition comprising a substantially purified IMPAH having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for stimulating cell proliferation comprising administering to a cell an effective amount of purified IMPAH.

The invention also provides a method for treating or preventing a disorder associated with cell proliferation comprising administering to a subject in need of such treatment an effective amount of an antagonist to IMPAH.

The invention also provides a method for treating or preventing a disorder associated with viral infection comprising administering to a subject in need of such treatment an effective amount of an antagonist to IMPAH.

The invention also provides a method for treating or preventing a disorder associated with immune response comprising administering to a subject in need of such treatment an effective amount of an antagonist to IMPAH.

The invention also provides a method for detecting a polynucleotide which encodes IMPAH in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding IMPAH in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of IMPAH. The alignment was produced using MACDNASIS PRO software (Hitachi Software Engineering Co. Ltd. San Bruno, Calif).

FIGS. 2A, 2B, 2C, and 2D show the amino acid sequence alignments among IMPAH (10403; SEQ ID NO:1), human importin alpha-3 (GI 1928975; SEQ ID NO:3), human importin alpha-1 (GI 1708480; SEQ ID NO:4), and human importin alpha-2 (GI 1708483; SEQ ID NO:5) produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

IMPAH, as used herein, refers to the amino acid sequences of substantially purified IMPAH obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to IMPAH, increases or prolongs the duration of the effect of IMPAH. Agonists may include proteins, nucleic acids, carbohydrates, or any other molecules which bind to and modulate the effect of IMPAH.

An "allele" or "allelic sequence", as used herein, is an alternative form of the gene encoding IMPAH. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding IMPAH as used herein include those with deletions, insertions, or substitutions of different nucleotides resulting in a polynucleotide that encodes the same or a functionally equivalent IMPAH. Included within this definition are polymorphisms which may or may not be readily detectable using a particular oligonucleotide probe of the polynucleotide encoding IMPAH, and improper or unexpected hybridization to alleles, with a locus other than the normal chromosomal locus for the polynucleotide sequence encoding IMPAH. The encoded protein may also be "altered" and contain deletions, insertions, or substitutions of amino acid residues which produce a silent change and result in a functionally equivalent IMPAH. Deliberate amino acid substitutions may be made on the basis of similarity in polarity, charge, solubility, hydrophobicity, hydrophilicity, and/or the amphipathic nature of the residues as long as the biological or immunological activity of IMPAH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of IMPAH are preferably about 5 to about 15 amino acids in length and retain the biological activity or the immunological activity of IMPAH. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to IMPAH, decreases the amount or the duration of the effect of the biological or immunological activity of IMPAH. Antagonists may include proteins, nucleic acids, carbohydrates, antibodies or any other molecules which decrease the effect of IMPAH.

As used herein, the term "antibody" refers to intact molecules as well as fragments thereof, such as Fab, F(ab')$_2$, and Fv, which are capable of binding the epitopic determinant. Antibodies that bind IMPAH polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic IMPAH, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by basepairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding IMPAH (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding IMPAH in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to IMPAH or the encoded IMPAH. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat. Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of IMPAH. For example, modulation may cause an increase or a decrease in protein activity, binding characteristics, or any other biological, functional or immunological properties of IMPAH.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length IMPAH and fragments thereof.

The term "sample", as used herein, is used in its broadest sense. A biological sample suspected of containing nucleic acid encoding IMPAH, or fragments thereof, or IMPAH itself may comprise a bodily fluid, extract from a cell, chromosome, organelle, or membrane isolated from a cell, a cell, genomic DNA, RNA, or cDNA (in solution or bound to a solid support), a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of IMPAH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human importin alpha homolog (hereinafter referred to as "IMPAH"), the polynucleotides encoding IMPAH, and the use of these compositions for the diagnosis, prevention, or treatment of disorders associated with cell proliferation, viral infection, and immune response.

Nucleic acids encoding the IMPAH of the present invention were first identified in Incyte Clone 10403 from the human leukemia-derived promonocyte cell line cDNA library THP1PLB01 using a computer search for amino acid sequence alignments. A consensus sequence, SEQ ID NO:2, was derived from the following overlapping and/or extended nucleic acid sequences: Incyte Clones 10403 (THP1PLB01), 1351853 (LATRTUT02), 2375259 (ISLTNOT01), and 2828354 (TLYMNOT03).

Figure 2A:
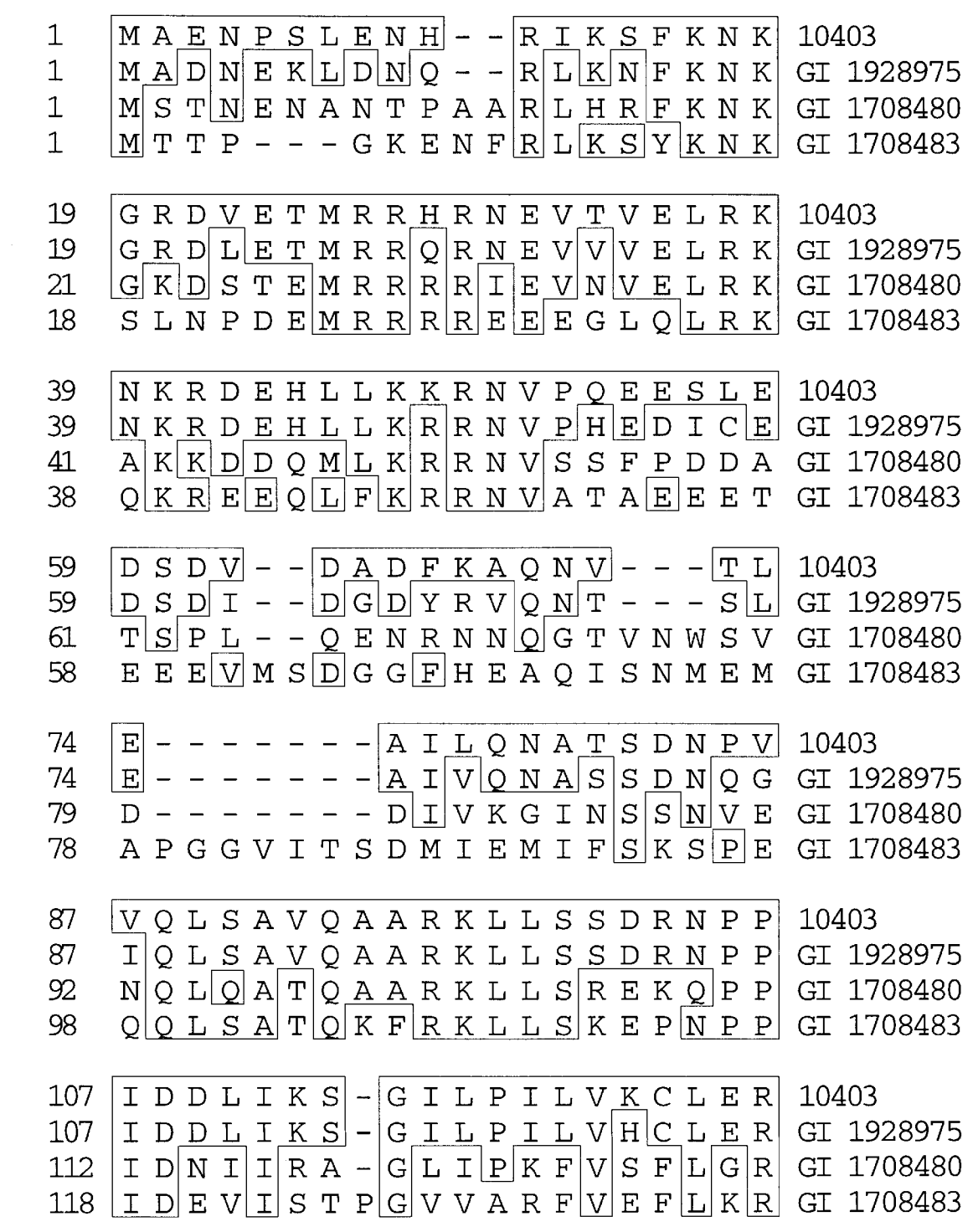
Figure 2B:
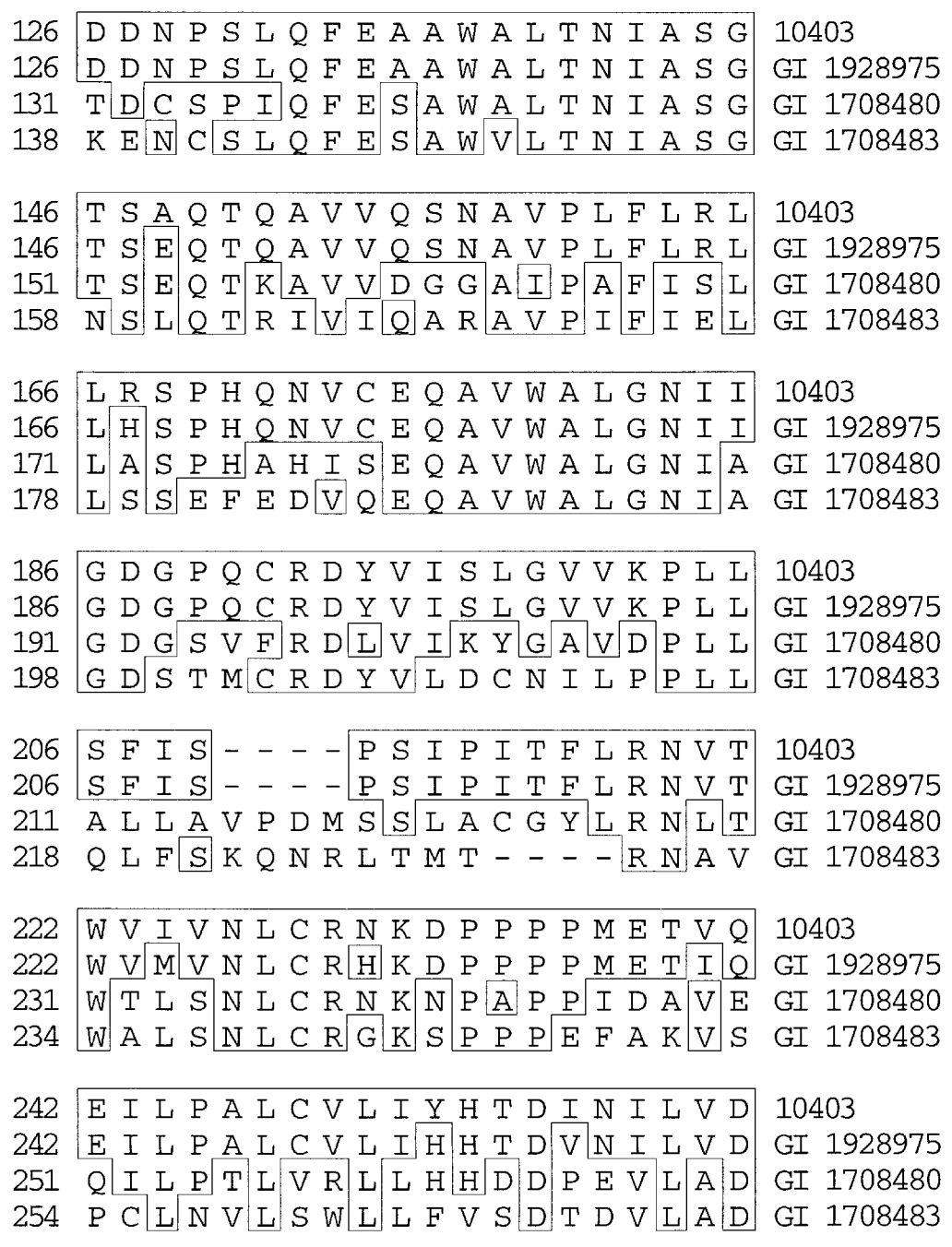
Figure 2C:
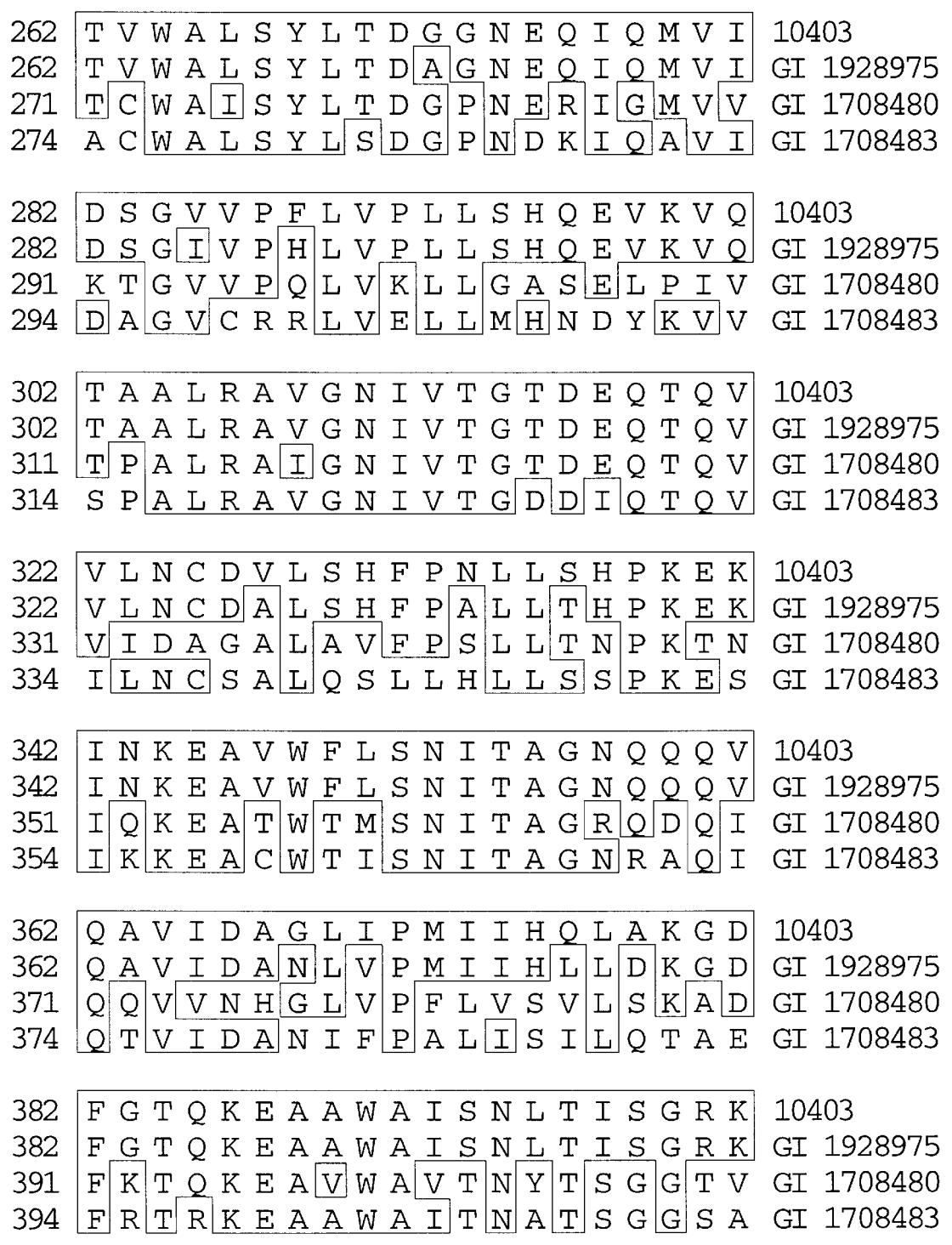
Figure 2D:
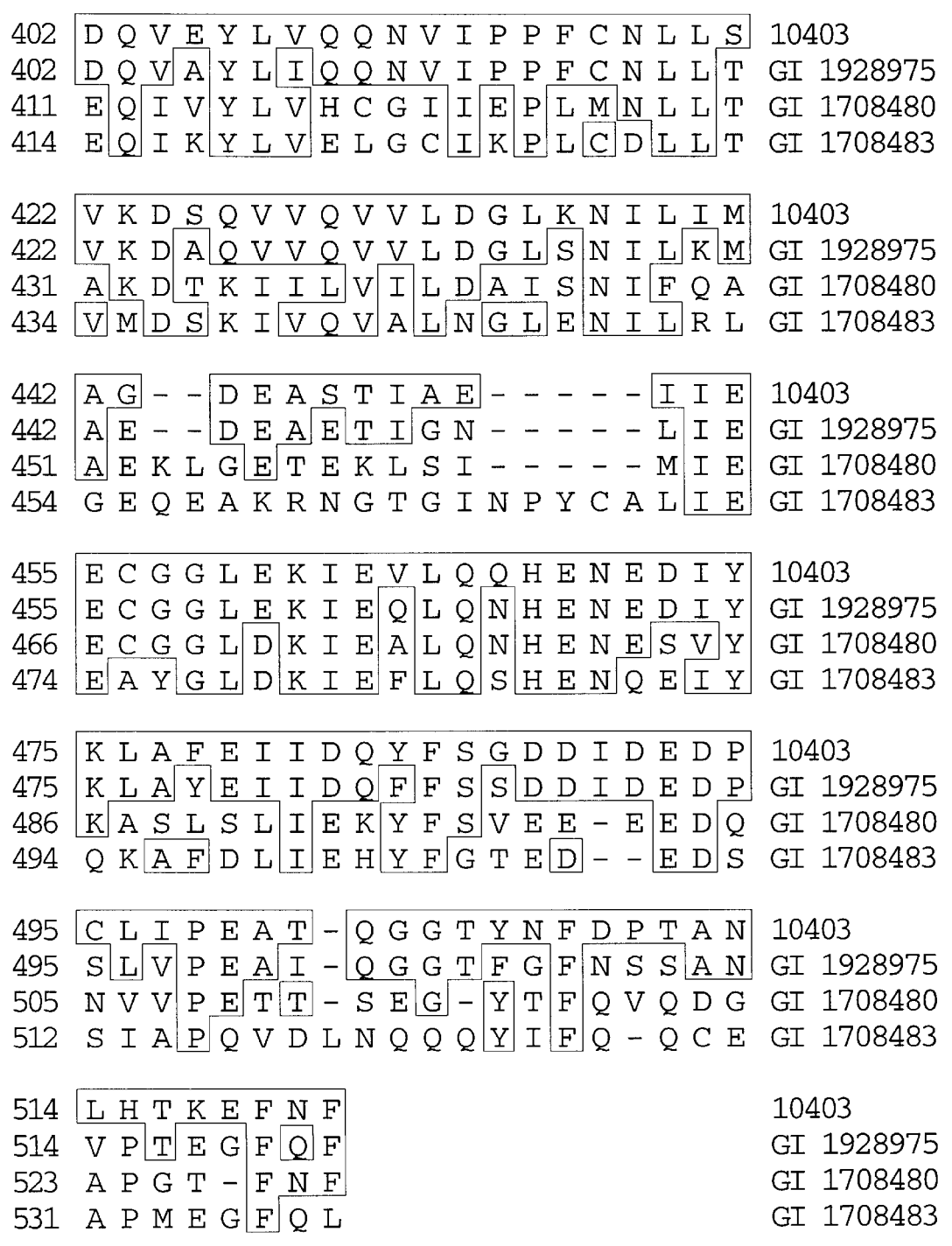

In one embodiment, the invention encompasses a polypeptide comprising the amino acid sequence of SEQ ID NO:1, as shown in Figs. 1A, 1B, 1C,1D, and 1E. IMPAH is 521 amino acids in length and has potential phosphorylation sites at residues S14, T24, S56, S60, S101, T239, S294, T313, T384, S398, S412, S421, S486, and T448. As shown in FIGS. 2A, 2B, 2C,and 2D, IMPAH has chemical and structural homology with human importin alpha-3 (GI 1928975; SEQ ID NO:3), human importin alpha-1 (GI 1708480; SEQ ID NO:4), and human importin alpha-2 (GI 1708483; SEQ ID NO:5). In particular, IMPAH and importin alpha-3 share 86% amino acid sequence identity; IMPAH and importin alpha-1 share 48% identity; and IMPAH and importin alpha-2 share 40% identity. Northern analysis shows the expression of IMPAH in various cell and tissues, including monocytes, promonocytes, lymphocytes, lymphoblasts, thymus, heart, lung, brain, a neuronal cell line, prostate, penis, and pancreas. Of particular note is the expression of IMPAH in tumor-associated tissues and in cells and tissues involved in hematopoiesis and immune response.

The invention also encompasses IMPAH variants. A preferred IMPAH variant is one having at least 80%, and more preferably at least 90%, amino acid sequence identity to the IMPAH amino acid sequence (SEQ ID NO:1) and which retains at least one biological, immunological or other functional characteristic or activity of IMPAH. A most preferred IMPAH variant is one having at least 95% amino acid sequence identity to SEQ ID NO:1.

The invention also encompasses polynucleotides which encode IMPAH. Accordingly, any nucleic acid sequence which encodes the amino acid sequence of IMPAH can be used to produce recombinant molecules which express IMPAH. In a particular embodiment, the invention encompasses the polynucleotide comprising the nucleic acid sequence of SEQ ID NO:2 as shown in Figs. 1A, 1B, 1C, 1D, and 1E.

It will be appreciated by those skilled in the art that as a result of the degeneracy of the genetic code, a multitude of nucleotide sequences encoding IMPAH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring IMPAH, and all such variations are to be considered as being specifically disclosed.

Although nucleotide sequences which encode IMPAH and its variants are preferably capable of hybridizing to the nucleotide sequence of the naturally occurring IMPAH under appropriately selected conditions of stringency, it may be advantageous to produce nucleotide sequences encoding IMPAH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding IMPAH and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode IMPAH and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding IMPAH or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (Gibco/BRL, Gaithersburg, Md.). Preferably, the process is automated with machines such as the MICROLAB 2200 (Hamilton, Reno, Nev.), peltier thermal cycler (PTC200; MJ Research, Watertown, Mass.) and the ABI CATALYST and 373 and 377 DNA sequencers (Perkin Elmer).

The nucleic acid sequences encoding IMPAH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENETYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode IMPAH may be used in recombinant DNA molecules to direct expression of IMPAH, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express IMPAH.

As will be understood by those of skill in the art, it may be advantageous to produce IMPAH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter IMPAH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding IMPAH may be ligated to a heterologous sequence to encode a fusion protein. For example, to screen peptide libraries for inhibitors of IMPAH activity, it may be useful to encode a chimeric IMPAH protein that can be recognized by a commercially available antibody. A fusion protein may also be engineered to contain a cleavage site located between the IMPAH encoding sequence and the heterologous protein sequence, so that IMPAH may be cleaved and purified away from the heterologous moiety.

In another embodiment, sequences encoding IMPAH may be synthesized, in whole or in part, using chemical methods well known in the art (see Caruthers, M. H. et al. (1980) Nucl. Acids Res. Symp. Ser. 215–223; Horn, T. et al. (1980) Nucl. Acids Res. Symp. Ser. 225–232). Alternatively, the protein itself may be produced using chemical methods to synthesize the amino acid sequence of IMPAH, or a fragment thereof. For example, peptide synthesis can be performed using various solid-phase techniques (Roberge, J. Y. et al. (1995) Science 269:202–204) and automated synthesis may be achieved, for example, using the ABI 43 1A peptide synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of IMPAH, or any part thereof, may be altered during direct synthesis and/or combined using chemical methods with sequences from other proteins, or any part thereof, to produce a variant polypeptide.

In order to express a biologically active IMPAH, the nucleotide sequences encoding IMPAH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding IMPAH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding IMPAH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding IMPAH, vectors based on SV40 or EBV may be used with an appropriate selectable marker.

In bacterial systems, a number of expression vectors may be selected depending upon the use intended for IMPAH. For example, when large quantities of IMPAH are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding IMPAH may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding IMPAH may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express IMPAH. For example, in one such system, *Autographa californica* nuclear polyhedrosis virus (AcNPV) is used as a vector to express foreign genes in *Spodoptera frugiperda* cells or in Trichoplusia larvae. The sequences encoding IMPAH may be cloned into a non-essential region of the virus, such as the polyhedrin gene, and placed under control of the polyhedrin promoter. Successful insertion of IMPAH will render the polyhedrin gene inactive and produce recombinant virus lacking coat protein. The recombinant viruses may then be used to infect, for example, S. frugiperda cells or Trichoplusia larvae in which IMPAH may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding IMPAH may be ligated into an adenovirus transcription/translation complex consisting of the late promoter and tripartite leader sequence. Insertion in a non-essential E1 or E3 region of the viral genome may be used to obtain a viable virus which is capable of expressing IMPAH in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding IMPAH. Such signals include the ATG initiation codon and adjacent sequences. In cases where sequences encoding IMPAH, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express IMPAH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding IMPAH is inserted within a marker gene sequence, transformed cells containing sequences encoding IMPAH can be identified by the absence of marker gene function. Alternatively, a marker gene can be placed in tandem with a sequence encoding IMPAH under the control of a single promoter. Expression of the marker gene in response to induction or selection usually indicates expression of the tandem gene as well.

Alternatively, host cells which contain the nucleic acid sequence encoding IMPAH and express IMPAH may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding IMPAH can be detected by DNA-DNA or DNA-RNA hybridization or amplification using probes or fragments or fragments of polynucleotides encoding IMPAH. Nucleic acid amplification based assays involve the use of oligonucleotides or oligomers based on the sequences encoding IMPAH to detect transformants containing DNA or RNA encoding IMPAH.

A variety of protocols for detecting and measuring the expression of IMPAH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on IMPAH is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding IMPAH include oligolabeling, nick translation, end-labeling or PCR amplification using a labeled nucleotide. Alternatively, the sequences encoding IMPAH, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding IMPAH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode IMPAH may be designed to contain signal sequences which direct secretion of IMPAH through a prokaryotic or eukaryotic cell membrane. Other constructions may be used to join sequences encoding IMPAH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and IMPAH may be used to facilitate purification. One such expression vector provides for expression of a fusion protein containing IMPAH and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying IMPAH from the fusion protein. A discussion of vectors which contain fusion proteins is provided in Kroll, D. J. et al. (1993; DNA Cell Biol. 12:441–453).

In addition to recombinant production, fragments of IMPAH may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of IMPAH may be chemically synthesized separately and combined using chemical methods to produce the full length molecule.

Therapeutics

Chemical and structural homology exists among IMPAH and the human importin homologs importin alpha-3 (GI 1928975; SEQ ID NO: 3), alpha-1 (GI 1708480; SEQ ID NO: 4), and alpha-2 (GI 1708483; SEQ ID NO: 5). In addition, IMPAH is expressed in tumor-associated tissues and in hematopoietic/immune cells and tissues. Therefore, IMPAH appears to play a role in disorders associated with cell proliferation, viral infection, and immune response.

In one embodiment, IMPAH or a fragment or derivative thereof may be added to cells to stimulate cell proliferation. In particular, IMPAH may be added to a cell or cells in vivo using delivery mechanisms such as liposomes, viral based vectors, or electroinjection for the purpose of promoting regeneration or cell differentiation of the cell or cells. In addition, IMPAH may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another embodiment, a vector capable of expressing IMPAH, or a fragment or a derivative thereof, may be administered to a cell or cells in vivo using delivery mechanisms, or to a cell to stimulate cell proliferation, as described above.

In still another embodiment, an agonist which modulates the activity of IMPAH may be administered to a cell to stimulate cell proliferation, as described above.

In one embodiment, an antagonist of IMPAH may be administered to a subject to prevent or treat a disorder associated with cell proliferation. Disorders of cell proliferation include but are not limited to cancers including adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds IMPAH may be used directly as an antagonist or indirectly as a targeting or delivery mechanism for bringing a pharmaceutical agent to cells or tissue which express IMPAH.

In another embodiment, a vector expressing the complement of the polynucleotide encoding IMPAH may be administered to a subject to treat or prevent a disorder associated with cell proliferation including, but not limited to, those described above.

In another embodiment, an antagonist of IMPAH may be administered to a subject to prevent or treat a disorder associated with viral infection. Disorders associated with viral infection include, but are not limited to, AIDS and Kaposi's sarcoma (HIV); T-cell lymphoma and T-cell leukemia (HTLV); mononucleosis and Burkitt's lymphoma (EBV); herpes (herpes simplex virus); chickenpox and shingles (Varicella-Zoster virus); rabies (rabies virus); smallpox (smallpox virus); respiratory viral diseases including the common cold, croup, influenza, laryngitis, pharyngitis, tracheobronchitis, and viral pneumonia (adenovirus, coronavirus, coxsackievirus, echovirus, influenza virus, parainfluenza virus, rhinovirus, and respiratory syncytial virus); and cancers (adenovirus, EBV, hepatitis B virus, polyomavirus, and papillomavirus). In one aspect, an antibody which specifically binds IMPAH may be used directly as an antagonist or indirectly as a targeting or delivery mechanism for bringing a pharmaceutical agent to cells or tissue which express IMPAH.

In another embodiment, a vector expressing the complement of the polynucleotide encoding IMPAH may be administered to a subject to treat or prevent a disorder associated with viral infection including, but not limited to, those described above.

In another embodiment, an antagonist of IMPAH may be administered to a subject to prevent or treat a disorder associated with immune response. Disorders associated with immune response include, but are not limited to, AIDS, Addison's disease, adult respiratory distress syndrome, allergies, anemia, asthma, arteriosclerosis, atherosclerosis, bronchitis, bursitis, cholecystitis, cirrhosis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, mixed connective tissue disease, multiple sclerosis, myasthenia gravis, myelofibrosis, myocardial or pericardial inflammation, osteoarthritis, osteoporosis, pancreatitis, psoriasis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds IMPAH may be used directly as an antagonist or indirectly as a targeting or delivery mechanism for bringing a pharmaceutical agent to cells or tissue which express IMPAH.

In another embodiment, a vector expressing the complement of the polynucleotide encoding IMPAH may be administered to a subject to treat or prevent a disorder associated with immune response including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of IMPAH may be produced using methods which are generally known in the art. In particular, purified IMPAH may be used to produce antibodies or to screen libraries of pharmaceutical agents to identify those which specifically bind IMPAH.

Antibodies to IMPAH may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with IMPAH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to IMPAH have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of IMPAH amino acids may be fused with those of another protein such as keyhole limpet hemocyanin and antibody produced against the chimeric molecule.

Monoclonal antibodies to IMPAH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce IMPAH-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for IMPAH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between IMPAH and its specific antibody. A two-site, monoclonal-based immunoassay utilizing monoclonal antibodies reactive to two non-interfering IMPAH epitopes is preferred, but a competitive binding assay may also be employed (Maddox, supra).

In another embodiment of the invention, the polynucleotides encoding IMPAH, or any fragment or complement thereof, may be used for therapeutic purposes. In one aspect, the complement of the polynucleotide encoding IMPAH may be used in situations in which it would be desirable to block the transcription of the mRNA. In particular, cells may be transformed with sequences complementary to polynucleotides encoding IMPAH. Thus, complementary molecules or fragments may be used to modulate IMPAH activity, or to achieve regulation of gene function. Such technology is now well known in the art, and sense or antisense oligonucleotides or larger fragments, can be designed from various locations along the coding or control regions of sequences encoding IMPAH.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding IMPAH. These techniques are described both in Sambrook et al. (supra) and in Ausubel et al. (supra).

Genes encoding IMPAH can be turned off by transforming a cell or tissue with expression vectors which express high levels of a polynucleotide or fragment thereof which encodes IMPAH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding IMPAH (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding IMPAH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding IMPAH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of IMPAH, antibodies to IMPAH, mimetics, agonists, antagonists, or inhibitors of IMPAH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of IMPAH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example IMPAH or fragments thereof, antibodies of IMPAH, agonists, antagonists or inhibitors of IMPAH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind IMPAH may be used for the diagnosis of conditions or diseases characterized by expression of IMPAH, or in assays to monitor patients being treated with IMPAH, agonists, antagonists or inhibitors. The antibodies useful for diagnostic purposes may be prepared in the same manner as those described above for therapeutics. Diagnostic assays for IMPAH include methods which utilize the antibody and a label to detect IMPAH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring IMPAH are known in the art and provide a basis for diagnosing altered or abnormal levels of IMPAH expression. Normal or standard values for IMPAH expression are established by combining body fluids or cell extracts taken from normal mammalian subjects, preferably human, with antibody to IMPAH under conditions suitable for complex formation. The amount of standard complex formation may be quantified by various methods, but preferably by photometric, means. Quantities of IMPAH expressed in subject samples from biopsied tissues are compared with the standard values. Deviation between standard and subject values establishes the parameters for diagnosing disease.

In another embodiment of the invention, the polynucleotides encoding IMPAH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of IMPAH may be correlated with disease. The diagnostic assay may be used to distinguish between absence, presence, and excess expression of IMPAH, and to monitor regulation of IMPAH levels during therapeutic intervention.

In one aspect, hybridization with PCR probes which are capable of detecting polynucleotide sequences, including genomic sequences, encoding IMPAH or closely related molecules, may be used to identify nucleic acid sequences which encode IMPAH. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding IMPAH, alleles, or related sequences.

Probes may also be used for the detection of related sequences, and should preferably contain at least 50% of the nucleotides from any of the IMPAH encoding sequences. The hybridization probes of the subject invention may be DNA or RNA and derived from the nucleotide sequence of SEQ ID NO:2 or from genomic sequence including promoter, enhancer elements, and introns of the naturally occurring IMPAH.

Means for producing specific hybridization probes for DNAs encoding IMPAH include the cloning of nucleic acid sequences encoding IMPAH or IMPAH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding IMPAH may be used for the diagnosis of conditions or disorders which are associated with expression of IMPAH. Examples of such conditions or disorders include: disorders associated with cell proliferation including adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders associated with viral infection including AIDS and Kaposi's sarcoma (HIV), T-cell lymphoma and T-cell leukemia (HTLV), mononucleosis and Burkitt's lymphoma (EBV), herpes (herpes simplex virus), chickenpox and shingles (Varicella-Zoster virus), rabies (rabies virus), smallpox (smallpox virus), respiratory viral diseases including the common cold, croup, influenza, laryngitis, pharyngitis, tracheobronchitis, and viral pneumonia (adenovirus, coronavirus, coxsackievirus, echovirus, influenza virus, parainfluenza virus, rhinovirus, and respiratory syncytial virus), cancer (adenovirus, EBV, hepatitis B virus, polyomavirus, and papillomavirus); and disorders associated with immune response including AIDS, Addison's disease, adult respiratory distress syndrome, allergies, anemia, asthma, arteriosclerosis, atherosclerosis, bronchitis, bursitis, cholecystitis, cirrhosis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, mixed connective tissue disease, multiple sclerosis, myasthenia gravis, myelofibrosis, myocardial or pericardial inflammation, osteoarthritis, osteoporosis, pancreatitis, psoriasis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. The polynucleotide sequences encoding IMPAH may be used in Southern or northern analysis, dot blot, or other membrane-based technologies; in PCR technologies; or in dipstick, pin, ELISA assays or microarrays utilizing fluids or tissues from patient biopsies to detect altered IMPAH expression. Such qualitative or quantitative methods are well known in the art.

In a particular aspect, the nucleotide sequences encoding IMPAH may be useful in assays that detect activation or induction of various cancers, particularly those mentioned above. The nucleotide sequences encoding IMPAH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding IMPAH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of IMPAH, a normal or standard profile for expression is established. This may be accomplished by combining body fluids or cell extracts taken from normal subjects, either animal or human, with a sequence, or a fragment thereof, which encodes IMPAH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding IMPAH may involve the use of PCR. Such oligomers may be chemically synthesized, generated enzymatically, or produced in vitro. Oligomers will preferably consist of two nucleotide sequences, one with sense orientation (5'->3') and another with antisense (3'<–5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of IMPAH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode IMPAH may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial PI constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding IMPAH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, IMPAH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between IMPAH and the agent being tested, may be measured.

Another technique for drug screening which may be used provides for high throughput screening of compounds having suitable binding affinity to the protein of interest as described in published PCT application WO84/03564. In this method, as applied to IMPAH large numbers of different small test compounds are synthesized on a solid substrate, such as plastic pins or some other surface. The test compounds are reacted with IMPAH, or fragments thereof, and washed. Bound IMPAH is then detected by methods well known in the art. Purified IMPAH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding IMPAH specifically compete with a test compound for binding IMPAH. In this manner, the antibodies can be used to detect the presence of any peptide which shares one or more antigenic determinants with IMPAH.

In additional embodiments, the nucleotide sequences which encode IMPAH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I THP1PLB01 cDNA Library Construction

The THP1PLB01 cDNA library was custom-constructed from activated human monocytes by Stratagene (Stratagene, La Jolla, Calif.). Poly(A+)RNA was purified from THP-1 cells which were cultured for 48 hr with 100 nm TPA and activated with 1 $\mu$g/ml LPS after 4 hr. cDNA synthesis was primed separately with both oligo d(T) and random hexamers and the two cDNA libraries were treated separately. Synthetic adaptor oligonucleotides were ligated onto cDNA ends enabling insertion into UNI-ZAP vector system (Stratagene). Finally, the two libraries were combined into a single library by mixing equal numbers of bacteriophage.

The cDNA library can be screened with either DNA probes or antibody probes and the PBLUESCRIPT phagemid (Stratagene) can be rapidly excised in vivo. The custom-constructed library phage particles were transfected into E. coli host strain, XL1-BLUE (Stratagene). Alternative unidirectional vectors include but are not limited to pcDNAI (Invitrogen, San Diego, Calif.) and PSHLOX-1 (Novagen, Madison, Wis.).

II Isolation and Sequencing of cDNA Clones

The phagemid forms of individual cDNA clones were obtained by the in vivo excision process, in which the host bacterial strain was coinfected with both the lambda library phage and an fl helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT plasmid and the cDNA insert.

The phagemid DNA was secreted from the cells, purified, and used to re-infect fresh host cells, where the double stranded phagemid DNA was produced. Because the phagemid carries the gene for β-lactamase, the newly-transformed bacteria are selected on medium containing ampicillin.

Phagemid DNA was purified using the MAGIC MINI-PREPS DNA Purification System (CATALOGUE #A7100; Promega, Madison, Wis.). The DNA was eluted from the purification resin already prepared for DNA sequencing and other analytical manipulations. Phagemid DNA was also purified using the QIAWELL-8 PLASMID, QIAWELL PLUS, AND QIAWELL ULTRA DNA purification system (QIAGEN, Chatsworth, Calif.). The DNA was eluted from the purification resin already prepared for DNA sequencing and other analytical manipulations.

The cDNA inserts from random isolates were sequenced in part. Conventional enzymatic methods employ DNA polymerase Klenow fragment, SEQUENASE or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labelled precursors) or by fluorescence (for fluorescent-labelled precursors). Recent improvements in mechanized reaction preparation, sequencing and analysis using the fluorescent detection method have permitted expansion in the number of sequences that can be determined per day (such as the Applied Biosystems 373 DNA sequencer and CATALYST 800).

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The findamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ™ (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\text{ sequence identity} \times \%\text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding IMPAH occurs. Abundance and percent abundance are also reported. Abundance directly reflects the number of times a particular transcript is represented in a cDNA library, and percent abundance is abundance divided by the total number of sequences examined in the cDNA library.

V Extension of IMPAH Encoding Polynucleotides

The nucleic acid sequence of the Incyte Clone 10403 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 μl of ligation buffer, 1μl T4-DNA ligase (15 units) and 1μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2x Carb. The following day, several colonies were randomly picked from each plate and cultured in 150 μl of liquid LB/2x Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.), hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the microarray.

VIII Complementary Polynucleotides

Sequence complementary to the IMPAH-encoding sequence, or any part thereof, is used to decrease or inhibit expression of naturally occurring IMPAH. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of IMPAH, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the IMPAH-encoding transcript.

IX Expression of IMPAH

Expression of IMPAH is accomplished by subcloning the cDNAs into appropriate vectors and transforming the vectors into host cells. In this case, the cloning vector is also used to express IMPAH in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of IMPAH into the bacterial growth media which can be used directly in the following assay for activity.

X Demonstration of IMPAH Activity

A nuclear import assay as described by Görlich, D. et al. (1994; Cell 79:767–778) is used to test the nuclear import activity of IMPAH. The import substrate is prepared by conjugating BSA with a peptide comprising the SV40 T-antigen NLS or an alternative NLS (e.g., as tabulated in Görlich and Mattaj (1996), supra) followed by fluorescein conjugation of the BSA-NLS. HeLa cells are permeabilized by digitonin, which permeabilizes the plasma membrane and leaves the nuclear membrane intact. The import reaction contains IMPAH, HeLa cytosol (previously depleted of importins by immunoprecipitation with importin-specific antibodies), import substrate, and other components as described by Görlich et al, supra. The import reaction is initiated by addition of digitonin-permeabilized cells and is allowed to proceed at room temperature for 60 min. Import activity is evaluated by fluorescence microscopy.

XI Production of IMPAH Specific Antibodies

IMPAH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using finoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring IMPAH Using Specific Antibodies

Naturally occurring or recombinant IMPAH is substantially purified by immunoaffinity chromatography using antibodies specific for IMPAH. An immunoaffinity column is constructed by covalently coupling IMPAH antibody to an activated chromatographic resin, such as CNBr-activated SEPHAROSE (Pharmacia & Upjohn). After the coupling, the resin is blocked and washed according to the manufacturer's instructions.

Media containing IMPAH is passed over the immunoaffinity column, and the column is washed under conditions that allow the preferential absorbance of IMPAH (e.g., high ionic strength buffers in the presence of detergent). The column is eluted under conditions that disrupt antibody/IMPAH binding (eg, a buffer of pH 2–3 or a high concentration of a chaotrope, such as urea or thiocyanate ion), and IMPAH is collected.

XIII Identification of Molecules Which Interact with IMPAH

IMPAH or biologically active fragments thereof are labeled with $^{25}$I Bolton-Hunter reagent (Bolton et al. (1973) Biochem. J. 133: 529). Candidate molecules previously arrayed in the wells of a multi-well plate are incubated with the labeled IMPAH, washed and any wells with labeled IMPAH complex are assayed. Data obtained using different concentrations of IMPAH are used to calculate values for the number, affinity, and association of IMPAH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A composition comprising the polynucleotide sequence of claim 1.

3. An isolated and purified polynucleotide sequence which is completely complementary to the polynucleotide sequence of claim 1.

4. An isolated and purified polynucleotide sequence comprising SEQ ID NO:2.

5. An isolated and purified polynucleotide sequence which is completely complementary to the polynucleotide sequence of claim 4.

6. An expression vector comprising the polynucleotide sequence of claim 1.

7. A host cell comprising the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

9. A method for detecting a polynucleotide encoding a polypeptide comprising the amino acid sequence of SEQ ID NO:1. in a biological sample comprising the steps of:

a) hybridizing the polynucleotide of claim 6 to nucleic acid material of a biological sample, thereby forming a hybridization complex; and b) detecting the hybridization complex, wherein the presence of the complex correlates with the presence of the polynucleotide encoding the polypeptide in the biological sample.

10. The method of claim 9 wherein the nucleic acid material is amplified by the polymerase chain reaction prior to hybridization.

\* \* \* \* \*

UNITED STATES PATENT AND TRADEMARK OFFICE
CERTIFICATE OF CORRECTION

PATENT NO. : 5,965,394
DATED : Oct. 12, 1999
INVENTOR(S) : Olga Bandman, Karl J. Guegler, Neil C. Corley, Purvi Shah It is certified that error appears in the above-identified patent and that said Letters Patent is hereby corrected as shown below:

Col. 51, line 7, deelete "claim 6" and insert --claim 3 --.

Signed and Sealed this

Ninth Day of January, 2001

Attest:

Attesting Officer

Q. TODD DICKINSON
Commissioner of Patents and Trademarks

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 521 amino acids
      (B) TYPE: amino acid
      (C) STRANDEDNESS: single
      (D) TOPOLOGY: linear (vii) IMMEDIATE SOURCE:
      (A) LIBRARY: THP1PLB01
      (B) CLONE: 10403

(xi) SEQUENCE DESCRIPTION: SEQ ID NO:1:

```
Met Ala Glu Asn Pro Ser Leu Glu Asn His Arg Ile Lys Ser Phe Lys
 1               5                  10                  15

Asn Lys Gly Arg Asp Val Glu Thr Met Arg Arg His Arg Asn Glu Val
            20                  25                  30

Thr Val Glu Leu Arg Lys Asn Lys Arg Asp Glu His Leu Leu Lys Lys
        35                  40                  45

Arg Asn Val Pro Gln Glu Glu Ser Leu Glu Asp Ser Asp Val Asp Ala
 50                  55                  60

Asp Phe Lys Ala Gln Asn Val Thr Leu Glu Ala Ile Leu Gln Asn Ala
 65                  70                  75                  80

Thr Ser Asp Asn Pro Val Val Gln Leu Ser Ala Val Gln Ala Ala Arg
                85                  90                  95

Lys Leu Leu Ser Ser Asp Arg Asn Pro Pro Ile Asp Asp Leu Ile Lys
            100                 105                 110

Ser Gly Ile Leu Pro Ile Leu Val Lys Cys Leu Glu Arg Asp Asp Asn
        115                 120                 125

Pro Ser Leu Gln Phe Glu Ala Ala Trp Ala Leu Thr Asn Ile Ala Ser
130                 135                 140

Gly Thr Ser Ala Gln Thr Gln Ala Val Val Gln Ser Asn Ala Val Pro
145                 150                 155                 160

Leu Phe Leu Arg Leu Leu Arg Ser Pro His Gln Asn Val Cys Glu Gln
                165                 170                 175

Ala Val Trp Ala Leu Gly Asn Ile Ile Gly Asp Gly Pro Gln Cys Arg
            180                 185                 190

Asp Tyr Val Ile Ser Leu Gly Val Val Lys Pro Leu Leu Ser Phe Ile
        195                 200                 205

Ser Pro Ser Ile Pro Ile Thr Phe Leu Arg Asn Val Thr Trp Val Ile
210                 215                 220

Val Asn Leu Cys Arg Asn Lys Asp Pro Pro Pro Met Glu Thr Val
225                 230                 235                 240

Gln Glu Ile Leu Pro Ala Leu Cys Val Leu Ile Tyr His Thr Asp Ile
                245                 250                 255

Asn Ile Leu Val Asp Thr Val Trp Ala Leu Ser Tyr Leu Thr Asp Gly
            260                 265                 270

Gly Asn Glu Gln Ile Gln Met Val Ile Asp Ser Gly Val Val Pro Phe
        275                 280                 285

Leu Val Pro Leu Leu Ser His Gln Glu Val Lys Val Gln Thr Ala Ala
290                 295                 300

Leu Arg Ala Val Gly Asn Ile Val Thr Gly Thr Asp Glu Gln Thr Gln
```

```
305                 310                 315                 320
Val Val Leu Asn Cys Asp Val Leu Ser His Phe Pro Asn Leu Leu Ser
                325                 330                 335

His Pro Lys Glu Lys Ile Asn Lys Glu Ala Val Trp Phe Leu Ser Asn
                340                 345                 350

Ile Thr Ala Gly Asn Gln Gln Gln Val Gln Ala Val Ile Asp Ala Gly
                355                 360                 365

Leu Ile Pro Met Ile Ile His Gln Leu Ala Lys Gly Asp Phe Gly Thr
        370                 375                 380

Gln Lys Glu Ala Ala Trp Ala Ile Ser Asn Leu Thr Ile Ser Gly Arg
385                 390                 395                 400

Lys Asp Gln Val Glu Tyr Leu Val Gln Gln Asn Val Ile Pro Pro Phe
                405                 410                 415

Cys Asn Leu Leu Ser Val Lys Asp Ser Gln Val Val Gln Val Val Leu
                420                 425                 430

Asp Gly Leu Lys Asn Ile Leu Ile Met Ala Gly Asp Glu Ala Ser Thr
        435                 440                 445

Ile Ala Glu Ile Ile Glu Glu Cys Gly Gly Leu Glu Lys Ile Glu Val
450                 455                 460

Leu Gln Gln His Glu Asn Glu Asp Ile Tyr Lys Leu Ala Phe Glu Ile
465                 470                 475                 480

Ile Asp Gln Tyr Phe Ser Gly Asp Asp Ile Asp Glu Asp Pro Cys Leu
                485                 490                 495

Ile Pro Glu Ala Thr Gln Gly Gly Thr Tyr Asn Phe Asp Pro Thr Ala
                500                 505                 510

Asn Leu His Thr Lys Glu Phe Asn Phe
        515                 520

(2) INFORMATION FOR SEQ ID NO:2:

(i) SEQUENCE CHARACTERISTICS:
        (A) LENGTH: 1733 base pairs
        (B) TYPE: nucleic acid
        (C) STRANDEDNESS: single
        (D) TOPOLOGY: linear (vii) IMMEDIATE SOURCE:
        (A) LIBRARY: THP1PLB01
        (B) CLONE: 10403

(xi) SEQUENCE DESCRIPTION: SEQ ID NO:2:

GCCGCCGGAG CCGCGCGCAG CCATGGCCGA GAACCCCAGC TTGGAGAACC ACCGCATCAA        60

GAGCTTCAAG AACAAGGGCC GCGATGTGGA ACAATGCGA AGACATAGAA ATGAAGTGAC        120

AGTGGAACTG CGGAAGAACA AAAGAGATGA ACACTTATTG AAAAAGAGAA ATGTTCCCCA      180

AGAAGAAAGT CTAGAAGATT CAGATGTTGA TGCTGATTTT AAAGCACAAA ATGTAACCCT      240

AGAAGCTATA TTGCAGAATG CCACAAGTGA TAACCCAGTG GTCCAATTGA GTGCTGTCCA      300

GGCAGCAAGA AAACTGTTAT CCAGTGACAG AAATCCACCG ATTGATGACT TAATAAAATC      360

TGGGATTTTA CCAATTCTAG TCAAATGTCT AGAAAGGGAT GATAATCCTT CATTACAGTT      420

TGAAGCTGCT TGGGCATTAA CTAACATAGC ATCAGGAACT TCTGCACAGA CTCAAGCTGT      480

TGTGCAGTCT AATGCAGTAC CTCTTTTTCT GAGACTTCTT CGTTCACCAC ATCAGAATGT      540

TTGTGAACAA GCAGTATGGG CTTTGGGAAA CATTATAGGT GATGGTCCTC AATGTAGAGA      600

TTATGTCATA TCACTGGGAG TTGTCAAACC TCTTCTGTCC TTCATCAGTC CTCCATCCC       660

CATCACCTTC CTTCGGAACG TCACATGGGT CATTGTCAAT CTCTGCAGGA ATAAGGATCC      720
```

```
CCCACCGCCT ATGGAGACAG TTCAGGAGAT TTTGCCAGCT TTATGTGTCC TCATATACCA     780

TACAGATATA AACATTCTTG TAGACACTGT TTGGGCTCTG TCATACTTGA CAGATGGAGG     840

TAATGAACAG ATACAGATGG TTATTGATTC AGGAGTTGTG CCCTTTCTTG TGCCCCTTCT     900

GAGCCATCAG GAAGTCAAAG TTCAAACAGC AGCCCTCAGA GCAGTTGGCA ACATAGTGAC     960

TGGCACCGAC GAGCAGACCC AGGTTGTTCT CAATTGTGAT GTCCTGTCAC ACTTCCCAAA    1020

TCTCTTATCA CACCCAAAAG AGAAGATAAA TAAGGAAGCA GTGTGGTTCC TTTCCAACAT    1080

AACAGCAGGC AACCAGCAAC AAGTTCAAGC TGTAATAGAT GCTGGATTAA TTCCTATGAT    1140

AATTCATCAG CTTGCTAAGG GGGACTTTGG AACACAAAAA GAAGCTGCTT GGGCAATCAG    1200

CAACTTAACA ATAAGTGGCA GAAAAGATCA GGTTGAGTAC CTTGTACAGC AGAATGTAAT    1260

ACCACCGTTC TGTAATTTAC TGTCAGTGAA AGATTCTCAA GTGGTTCAGG TGGTTCTAGA    1320

TGGTCTAAAA AACATTCTGA TAATGGCCGG TGATGAAGCA AGCACAATAG CTGAAATAAT    1380

AGAGGAATGT GGAGGTTTGG AGAAAATTGA AGTTTTACAG CAACATGAAA ATGAAGACAT    1440

ATATAAATTA GCATTTGAAA TCATAGATCA GTATTTCTCT GGTGATGATA TTGATGAAGA    1500

TCCCTGCCTC ATTCCTGAAG CAACACAAGG AGGTACCTAC AATTTTGATC AACAGCCAA    1560

CCTTCACACA AAAGAATTTA ATTTTTAAAT TCAGTTGAGT GCAGCATCTT TCCCACATTC    1620

AATATGAAGC ACCACCAGAT GGCTACCAAA TGATAAGAAC ACAGCCACAA AAAGCTCCCA    1680

AACACACATG CCTCTTTGGT TTGATGCTTC TAAGGCAGCC ATGTCTCAGC CCT           1733
```

(2) INFORMATION FOR SEQ ID NO:3:

(i) SEQUENCE CHARACTERISTICS:
        (A) LENGTH: 521 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1928975

(xi) SEQUENCE DESCRIPTION: SEQ ID NO:3:

```
Met Ala Asp Asn Glu Lys Leu Asp Asn Gln Arg Leu Lys Asn Phe Lys
  1               5                  10                  15

Asn Lys Gly Arg Asp Leu Glu Thr Met Arg Arg Gln Arg Asn Glu Val
             20                  25                  30

Val Val Glu Leu Arg Lys Asn Lys Arg Asp Glu His Leu Leu Lys Arg
         35                  40                  45

Arg Asn Val Pro His Glu Asp Ile Cys Glu Asp Ser Asp Ile Asp Gly
 50                  55                  60

Asp Tyr Arg Val Gln Asn Thr Ser Leu Glu Ala Ile Val Gln Asn Ala
 65                  70                  75                  80

Ser Ser Asp Asn Gln Gly Ile Gln Leu Ser Ala Val Gln Ala Ala Arg
                 85                  90                  95

Lys Leu Leu Ser Ser Asp Arg Asn Pro Pro Ile Asp Asp Leu Ile Lys
            100                 105                 110

Ser Gly Ile Leu Pro Ile Leu Val His Cys Leu Glu Arg Asp Asp Asn
        115                 120                 125

Pro Ser Leu Gln Phe Glu Ala Ala Trp Ala Leu Thr Asn Ile Ala Ser
    130                 135                 140

Gly Thr Ser Glu Gln Thr Gln Ala Val Val Gln Ser Asn Ala Val Pro
145                 150                 155                 160

Leu Phe Leu Arg Leu Leu His Ser Pro His Gln Asn Val Cys Glu Gln
```

```
                    165                 170                 175
Ala Val Trp Ala Leu Gly Asn Ile Ile Gly Asp Gly Pro Gln Cys Arg
            180                 185                 190

Asp Tyr Val Ile Ser Leu Gly Val Val Lys Pro Leu Leu Ser Phe Ile
            195                 200                 205

Ser Pro Ser Ile Pro Ile Thr Phe Leu Arg Asn Val Thr Trp Val Met
210                 215                 220

Val Asn Leu Cys Arg His Lys Asp Pro Pro Pro Met Glu Thr Ile
225                 230                 235                 240

Gln Glu Ile Leu Pro Ala Leu Cys Val Leu Ile His His Thr Asp Val
                245                 250                 255

Asn Ile Leu Val Asp Thr Val Trp Ala Leu Ser Tyr Leu Thr Asp Ala
                260                 265                 270

Gly Asn Glu Gln Ile Gln Met Val Ile Asp Ser Gly Ile Val Pro His
                275                 280                 285

Leu Val Pro Leu Leu Ser His Gln Glu Val Lys Val Gln Thr Ala Ala
290                 295                 300

Leu Arg Ala Val Gly Asn Ile Val Thr Gly Thr Asp Glu Gln Thr Gln
305                 310                 315                 320

Val Val Leu Asn Cys Asp Ala Leu Ser His Phe Pro Ala Leu Leu Thr
                325                 330                 335

His Pro Lys Glu Lys Ile Asn Lys Glu Ala Val Trp Phe Leu Ser Asn
                340                 345                 350

Ile Thr Ala Gly Asn Gln Gln Val Gln Ala Val Ile Asp Ala Asn
                355                 360                 365

Leu Val Pro Met Ile Ile His Leu Leu Asp Lys Gly Asp Phe Gly Thr
370                 375                 380

Gln Lys Glu Ala Ala Trp Ala Ile Ser Asn Leu Thr Ile Ser Gly Arg
385                 390                 395                 400

Lys Asp Gln Val Ala Tyr Leu Ile Gln Gln Asn Val Ile Pro Pro Phe
                405                 410                 415

Cys Asn Leu Leu Thr Val Lys Asp Ala Gln Val Val Gln Val Val Leu
                420                 425                 430

Asp Gly Leu Ser Asn Ile Leu Lys Met Ala Glu Asp Glu Ala Glu Thr
                435                 440                 445

Ile Gly Asn Leu Ile Glu Glu Cys Gly Gly Leu Glu Lys Ile Glu Gln
450                 455                 460

Leu Gln Asn His Glu Asn Glu Asp Ile Tyr Lys Leu Ala Tyr Glu Ile
465                 470                 475                 480

Ile Asp Gln Phe Phe Ser Ser Asp Asp Ile Asp Glu Asp Pro Ser Leu
                485                 490                 495

Val Pro Glu Ala Ile Gln Gly Gly Thr Phe Gly Phe Asn Ser Ser Ala
                500                 505                 510

Asn Val Pro Thr Glu Gly Phe Gln Phe
                515                 520
```

(2) INFORMATION FOR SEQ ID NO:4:

(i) SEQUENCE CHARACTERISTICS:
        (A) LENGTH: 529 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1708480

(xi) SEQUENCE DESCRIPTION: SEQ ID NO:4:

```
Met Ser Thr Asn Glu Asn Ala Asn Thr Pro Ala Ala Arg Leu His Arg
 1               5                  10                  15

Phe Lys Asn Lys Gly Lys Asp Ser Thr Glu Met Arg Arg Arg Arg Ile
                20                  25                  30

Glu Val Asn Val Glu Leu Arg Lys Ala Lys Lys Asp Asp Gln Met Leu
                35                  40                  45

Lys Arg Arg Asn Val Ser Ser Phe Pro Asp Asp Ala Thr Ser Pro Leu
 50                  55                  60

Gln Glu Asn Arg Asn Asn Gln Gly Thr Val Asn Trp Ser Val Asp Asp
 65                  70                  75                  80

Ile Val Lys Gly Ile Asn Ser Ser Asn Val Glu Asn Gln Leu Gln Ala
                    85                  90                  95

Thr Gln Ala Ala Arg Lys Leu Leu Ser Arg Glu Lys Gln Pro Pro Ile
                   100                 105                 110

Asp Asn Ile Ile Arg Ala Gly Leu Ile Pro Lys Phe Val Ser Phe Leu
                   115                 120                 125

Gly Arg Thr Asp Cys Ser Pro Ile Gln Phe Glu Ser Ala Trp Ala Leu
             130                 135                 140

Thr Asn Ile Ala Ser Gly Thr Ser Glu Gln Thr Lys Ala Val Val Asp
145                 150                 155                 160

Gly Gly Ala Ile Pro Ala Phe Ile Ser Leu Leu Ala Ser Pro His Ala
                165                 170                 175

His Ile Ser Glu Gln Ala Val Trp Ala Leu Gly Asn Ile Ala Gly Asp
                180                 185                 190

Gly Ser Val Phe Arg Asp Leu Val Ile Lys Tyr Gly Ala Val Asp Pro
            195                 200                 205

Leu Leu Ala Leu Leu Ala Val Pro Asp Met Ser Ser Leu Ala Cys Gly
210                 215                 220

Tyr Leu Arg Asn Leu Thr Trp Thr Leu Ser Asn Leu Cys Arg Asn Lys
225                 230                 235                 240

Asn Pro Ala Pro Pro Ile Asp Ala Val Glu Gln Ile Leu Pro Thr Leu
                245                 250                 255

Val Arg Leu Leu His His Asp Pro Glu Val Leu Ala Asp Thr Cys
            260                 265                 270

Trp Ala Ile Ser Tyr Leu Thr Asp Gly Pro Asn Glu Arg Ile Gly Met
            275                 280                 285

Val Val Lys Thr Gly Val Val Pro Gln Leu Val Lys Leu Leu Gly Ala
290                 295                 300

Ser Glu Leu Pro Ile Val Thr Pro Ala Leu Arg Ala Ile Gly Asn Ile
305                 310                 315                 320

Val Thr Gly Thr Asp Glu Gln Thr Gln Val Val Ile Asp Ala Gly Ala
                325                 330                 335

Leu Ala Val Phe Pro Ser Leu Leu Thr Asn Pro Lys Thr Asn Ile Gln
                340                 345                 350

Lys Glu Ala Thr Trp Thr Met Ser Asn Ile Thr Ala Gly Arg Gln Asp
                355                 360                 365

Gln Ile Gln Gln Val Val Asn His Gly Leu Val Pro Phe Leu Val Ser
                370                 375                 380

Val Leu Ser Lys Ala Asp Phe Lys Thr Gln Lys Glu Ala Val Trp Ala
385                 390                 395                 400

Val Thr Asn Tyr Thr Ser Gly Gly Thr Val Glu Gln Ile Val Tyr Leu
                405                 410                 415
```

```
Val His Cys Gly Ile Ile Glu Pro Leu Met Asn Leu Leu Thr Ala Lys
            420                 425                 430

Asp Thr Lys Ile Ile Leu Val Ile Leu Asp Ala Ile Ser Asn Ile Phe
            435                 440                 445

Gln Ala Ala Glu Lys Leu Gly Glu Thr Glu Lys Leu Ser Ile Met Ile
            450                 455                 460

Glu Glu Cys Gly Gly Leu Asp Lys Ile Glu Ala Leu Gln Asn His Glu
465                 470                 475                 480

Asn Glu Ser Val Tyr Lys Ala Ser Leu Ser Leu Ile Glu Lys Tyr Phe
            485                 490                 495

Ser Val Glu Glu Glu Asp Gln Asn Val Val Pro Glu Thr Thr Ser
            500                 505                 510

Glu Gly Tyr Thr Phe Gln Val Gln Asp Gly Ala Pro Gly Thr Phe Asn
            515                 520                 525

Phe
```

(2) INFORMATION FOR SEQ ID NO:5:

(i) SEQUENCE CHARACTERISTICS:
　　　　　　(A) LENGTH: 538 amino acids
　　　　　　(B) TYPE: amino acid
　　　　　　(C) STRANDEDNESS: single
　　　　　　(D) TOPOLOGY: linear (vii) IMMEDIATE SOURCE:
　　　　　　(A) LIBRARY: GenBank
　　　　　　(B) CLONE: 1708483

(xi) SEQUENCE DESCRIPTION: SEQ ID NO:5:

```
Met Thr Thr Pro Gly Lys Glu Asn Phe Arg Leu Lys Ser Tyr Lys Asn
1               5                   10                  15

Lys Ser Leu Asn Pro Asp Glu Met Arg Arg Arg Glu Glu Glu Glu Gly
            20                  25                  30

Leu Gln Leu Arg Lys Gln Lys Arg Glu Glu Gln Leu Phe Lys Arg Arg
            35                  40                  45

Asn Val Ala Thr Ala Glu Glu Thr Glu Glu Glu Val Met Ser Asp
50                  55                  60

Gly Gly Phe His Glu Ala Gln Ile Ser Asn Met Glu Met Ala Pro Gly
65                  70                  75                  80

Gly Val Ile Thr Ser Asp Met Ile Glu Met Ile Phe Ser Lys Ser Pro
            85                  90                  95

Glu Gln Gln Leu Ser Ala Thr Gln Lys Phe Arg Lys Leu Leu Ser Lys
            100                 105                 110

Glu Pro Asn Pro Pro Ile Asp Glu Val Ile Ser Thr Pro Gly Val Val
            115                 120                 125

Ala Arg Phe Val Glu Phe Leu Lys Arg Lys Glu Asn Cys Ser Leu Gln
            130                 135                 140

Phe Glu Ser Ala Trp Val Leu Thr Asn Ile Ala Ser Gly Asn Ser Leu
145                 150                 155                 160

Gln Thr Arg Ile Val Ile Gln Ala Arg Ala Val Pro Ile Phe Ile Glu
            165                 170                 175

Leu Leu Ser Ser Glu Phe Glu Asp Val Gln Glu Gln Ala Val Trp Ala
            180                 185                 190

Leu Gly Asn Ile Ala Gly Asp Ser Thr Met Cys Arg Asp Tyr Val Leu
            195                 200                 205

Asp Cys Asn Ile Leu Pro Pro Leu Leu Gln Leu Phe Ser Lys Gln Asn
210                 215                 220
```

```
Arg Leu Thr Met Thr Arg Asn Ala Val Trp Ala Leu Ser Asn Leu Cys
225             230                 235                 240

Arg Gly Lys Ser Pro Pro Glu Phe Ala Lys Val Ser Pro Cys Leu
            245                 250                 255

Asn Val Leu Ser Trp Leu Leu Phe Val Ser Asp Thr Asp Val Leu Ala
            260                 265                 270

Asp Ala Cys Trp Ala Leu Ser Tyr Leu Ser Asp Gly Pro Asn Asp Lys
        275                 280                 285

Ile Gln Ala Val Ile Asp Ala Gly Val Cys Arg Arg Leu Val Glu Leu
        290                 295                 300

Leu Met His Asn Asp Tyr Lys Val Val Ser Pro Ala Leu Arg Ala Val
305                 310                 315                 320

Gly Asn Ile Val Thr Gly Asp Asp Ile Gln Thr Val Ile Leu Asn
                325                 330                 335

Cys Ser Ala Leu Gln Ser Leu Leu His Leu Leu Ser Ser Pro Lys Glu
            340                 345                 350

Ser Ile Lys Lys Glu Ala Cys Trp Thr Ile Ser Asn Ile Thr Ala Gly
            355                 360                 365

Asn Arg Ala Gln Ile Gln Thr Val Ile Asp Ala Asn Ile Phe Pro Ala
    370                 375                 380

Leu Ile Ser Ile Leu Gln Thr Ala Glu Phe Arg Thr Arg Lys Glu Ala
385                 390                 395                 400

Ala Trp Ala Ile Thr Asn Ala Thr Ser Gly Gly Ser Ala Glu Gln Ile
                405                 410                 415

Lys Tyr Leu Val Glu Leu Gly Cys Ile Lys Pro Leu Cys Asp Leu Leu
                420                 425                 430

Thr Val Met Asp Ser Lys Ile Val Gln Val Ala Leu Asn Gly Leu Glu
            435                 440                 445

Asn Ile Leu Arg Leu Gly Glu Gln Glu Ala Lys Arg Asn Gly Thr Gly
    450                 455                 460

Ile Asn Pro Tyr Cys Ala Leu Ile Glu Glu Ala Tyr Gly Leu Asp Lys
465                 470                 475                 480

Ile Glu Phe Leu Gln Ser His Glu Asn Gln Glu Ile Tyr Gln Lys Ala
            485                 490                 495

Phe Asp Leu Ile Glu His Tyr Phe Gly Thr Glu Asp Glu Asp Ser Ser
            500                 505                 510

Ile Ala Pro Gln Val Asp Leu Asn Gln Gln Gln Tyr Ile Phe Gln Gln
        515                 520                 525

Cys Glu Ala Pro Met Glu Gly Phe Gln Leu
530                 535
```